(12) United States Patent
Chung et al.

(10) Patent No.: US 11,927,559 B1
(45) Date of Patent: Mar. 12, 2024

(54) GAS SAMPLING BAG FOR GAS PH MEASUREMENT

(71) Applicant: UltraE Co. Ltd., Taichung (TW)

(72) Inventors: Hsieh-Hsun Chung, Taichung (TW); Ping-Hsi Hsieh, Taichung (TW)

(73) Assignee: ULTRAE CO. LTD., Taichung (TW)

( * ) Notice: Subject to any disclaimer, the term of this patent is extended or adjusted under 35 U.S.C. 154(b) by 0 days.

(21) Appl. No.: 17/974,772

(22) Filed: Oct. 27, 2022

(30) Foreign Application Priority Data

Aug. 31, 2022 (TW) .................................. 111133000

(51) Int. Cl.
*G01N 27/327* (2006.01)
*G01N 27/30* (2006.01)

(52) U.S. Cl.
CPC ....... *G01N 27/3272* (2013.01); *G01N 27/301* (2013.01)

(58) Field of Classification Search
CPC ........... A61B 5/093; A61B 5/08; A61B 5/091; A61B 5/097; A61B 5/14; A61B 5/1405; A61B 5/1444; A61B 5/145; A61B 5/14539; A61B 5/14542; A61B 5/14551; G01N 27/3272; G01N 27/301; G01N 27/4166; G01N 27/4167; G01N 27/302; G01N 27/333; G01N 27/3335; G01N 27/416

See application file for complete search history.

(56) References Cited

U.S. PATENT DOCUMENTS

| | | | |
|---|---|---|---|
| 4,474,648 A | 10/1984 | Tantram et al. | |
| 2017/0273603 A1 | 8/2017 | Suri et al. | |
| 2021/0177303 A1* | 6/2021 | Pimentel | ................ A61B 5/742 |

FOREIGN PATENT DOCUMENTS

| | | | | |
|---|---|---|---|---|
| CN | 101074963 A | 11/2007 | | |
| CN | 101458225 A | 6/2009 | | |
| CN | 110261458 A | 9/2019 | | |
| EP | 0734520 A1 | 10/1996 | | |
| KR | 20210091857 A | * | 1/2020 | ........... A61B 5/4845 |

OTHER PUBLICATIONS

English Machine Translation of KR 20210091857 (Year: 2021).*

* cited by examiner

*Primary Examiner* — Gurpreet Kaur
(74) *Attorney, Agent, or Firm* — MUNCY, GEISSLER, OLDS & LOWE, PC

(57) ABSTRACT

A gas sampling bag for gas pH measurement includes a main sampling chamber and an electrochemical test strip accommodating chamber for accommodating an electrochemical test strip. The electrochemical test strip includes a strip body, a working electrode, a pH sensing layer, a reference electrode and a solid water absorption layer. The working electrode has a first part located in a detection area of the strip body. The pH sensing layer is formed on the first part. The reference electrode has a second part located in the detection area. The solid water absorbing layer is formed on the detection area and covers the pH sensing layer and the second part. The solid water absorbing layer is used for absorbing or adsorbing water in the gas sample to form an electrical connection between the first and second parts.

9 Claims, 15 Drawing Sheets

GAS SAMPLING BAG FOR GAS PH MEASUREMENT

BACKGROUND OF THE INVENTION

1. Technical Field

The present invention relates to a gas pH measurement technology, and more particularly to a gas sampling bag for gas pH measurement.

2. Description of Related Art

Conventional pH measuring devices and pH test strips are used to measure pH values of aqueous solutions, but they cannot be used to measure pH values of gas samples.

In the prior art, in order to measure the pH value of a gas, a gas sample needs to be collected first and then introduced into an aqueous solution so that water-soluble substances in the gas sample can be dissolved in the aqueous solution. This is when the conventional pH measuring devices or pH test strips can be used to measure the pH value of the aqueous solution.

However, there are some defects aroused from the above-mentioned conventional method. The pH value measured can only represent the pH value at the moment the gas sample is acquired. Continuous pH monitor cannot be achieved with the above-mentioned conventional method, especially in environments where the pH values thereof constantly vary. Besides, the step to introduce gas sample into aqueous solution makes the conventional method harder to be implemented.

BRIEF SUMMARY OF THE INVENTION

The primary objective of the present invention is to provide a gas sampling bag for gas pH measurement.

To achieve the foregoing and other objectives, the present invention provides a gas sampling bag for gas pH measurement that includes a bag body. The bag body includes a main sampling chamber, an electrochemical test strip accommodating chamber and a blowpipe. The blowpipe has a gas channel in communication with the main sampling chamber. The electrochemical test strip accommodating chamber is in communication with the main sampling chamber and is adapted to accommodate an electrochemical test strip, which includes a strip body, a working electrode, a pH sensing layer, a reference electrode and a solid water absorption layer. The strip body has a detection area for contact with a gas sample. The working electrode is disposed on the strip body and has a first part located in the detection area. The pH sensing layer is disposed on the first part of the working electrode located in the detection area. The reference electrode is disposed on the strip body and has a second part located in the detection area. The solid water absorption layer is disposed in the detection area and covers the pH sensing layer and the second part. The solid water absorption layer is adapted to absorb or adsorb water in the gas sample in a manner that the first and second parts are electrically connected to each other.

The gas sampling bag of the present invention can be used to collect gas sample. By additionally forming a solid water absorption layer in the detection area of the electrochemical test strip, the solid water absorption layer can directly absorb/adsorb the water in the gas sample (water vapor), so that the first and second parts can form an electrical connection without adding water droplets in the detection area and without introducing the gas sample into an aqueous solution. In addition, the solid water absorbing layer can dynamically absorb/desorb water-soluble substances in the gas sample, meaning continuous pH monitor can be possible. After the water-soluble substances interact with the pH sensing layer, a potential difference can be generated between the working electrode and the reference electrode, based on which the pH value of the gas sample can be measured.

DETAILED DESCRIPTION OF THE INVENTION

Figure 1:
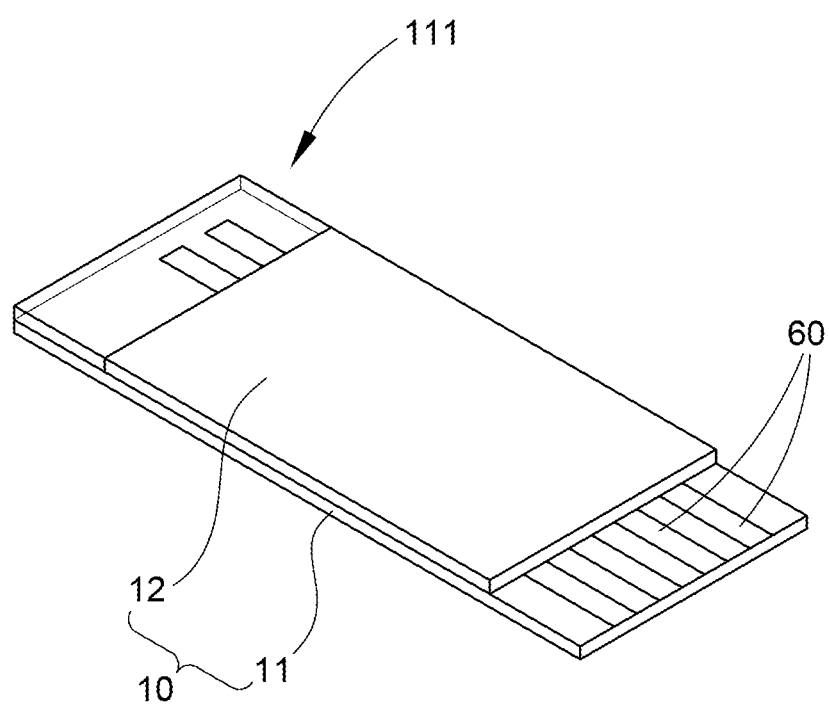
FIG. 1 is a perspective view of a first embodiment of the present invention.
Figure 2:
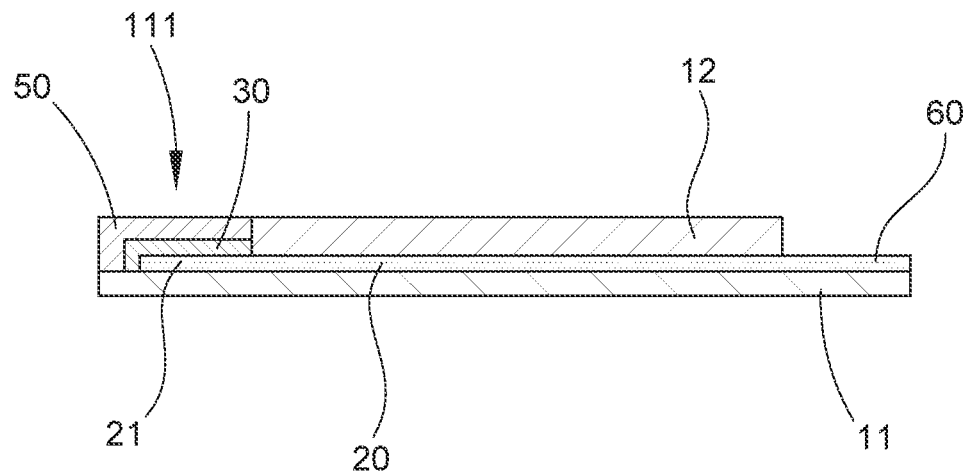
FIG. 2 is a 2-2 profile of FIG. 1.
Figure 3:
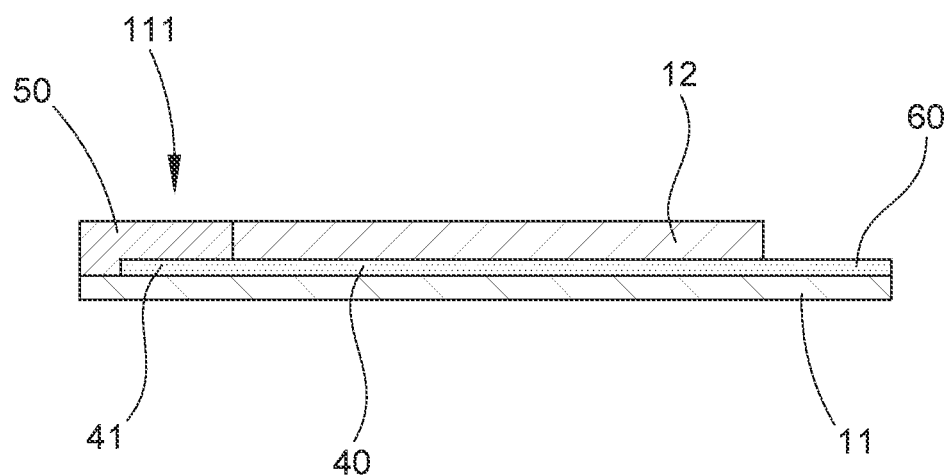
FIG. 3 is a 3-3 profile of FIG. 1.

Referring to FIGS. 1-2 for an electrochemical test strip of the first embodiment of the present invention. The electrochemical test strip has a strip body 10, a working electrode 20, a pH sensing layer 30, a reference electrode 40, a solid water absorption layer 50 and a plurality of gold fingers 60. The electrochemical test strip of the present invention can be used to measure pH values of gas samples.

The strip body 10 includes a substrate 11 and a protection layer 12 and has a detection area 111. The working electrode 20, the reference electrode 40 and the gold fingers 60 is disposed on the substrate 11 of the strip body 10. The protection layer 12 is disposed on the substrate 11 and covers a part of the working electrode 20 and a part of the reference electrode 40. Both distal ends of the substrate 11 are not covered by the protection layer 12. One of the distal ends constitute the detection area 111 and can be in contact with gas samples. The other of the distal ends exposes the gold fingers 60, which means the gold fingers 60 is not located in the detection area 111. The working electrode 20 has a first part 21 located in the detection area 111, and the reference electrode 40 has a second part 41 located in the detection area 111 as well. The gold fingers 60 are electrically connected to the working electrode 20 and the reference electrode 40, respectively. Some of the gold fingers 60 may be electrically connected to other electrodes disposed on the strip body 10, if any.

The pH sensing layer 30 covers and is formed on the first part 21 of the working electrode 20. The pH sensing layer 30 may be made of pH sensing materials such as aniline compounds (such as aniline and clenbuterol), aromatic heterocyclic compounds (such as melamine, lamotrigine and altretamine), aminophenols (such as acetaminophen), metal oxides (such as copper oxide, iridium oxide), azo compounds (such as azobenzene) or conductive polymers (such as Nafion and polypyrrole). These pH sensing materials have bonding sites which are adsorbable/desorbable with hydrogen ions. When these bonding sites adsorb/desorb hydrogen ions, their chemical potentials will vary.

The solid water absorption layer 50 is located in the detection area 111 and covers the pH sensing layer 30 and the second part 41 of the reference electrode 40. The solid water absorption layer 50 is adapted to absorb or adsorb water in the gas sample (water vapor) so that the first and second parts 21 and 41 can be electrically connected to each other. The solid water absorption layer 50 can be, but not limited to, water-absorbing surfactants, humectants, antioxidants, thickeners, conductive polymers or mixtures thereof. The water-absorbing surfactants can be cetyltrimethyl ammonium chloride (CTAC). The humectants can be sorbitol, PCA-Na, 1,3-propanediol, co-enzyme Q10, ceramide, allantoin, collagen, hyaluronic acid, urea, glycerin or polyethylene glycol. The antioxidants can be Vitamin C or 3,4-dihydroxy-cinnamic acid. The thickeners can be methylcellulose, carboxylmethyl cellulose sodium salt (CMC) or polyvinyl alcohol. The conductive polymers can be Nafion or poly acryl sodium (PAS). In a single electrochemical test strip, the pH sensing layer 30 and the solid water absorption layer 50 are made of different materials.

When measuring pH of gas, the electrochemical test strip can be brought in contact with the gas sample. The solid water absorption layer 50 will start to absorb/adsorb water (in the form of water vapor for instance). The absorbed/adsorbed water plays two roles, one of which is to enable the working electrode 20 and the reference electrode 40 to electrically connect to each other, while the other of which is to dynamically adsorb/desorb water-soluble pH substances originally contained in the gas test sample in vaporized form, if any, until the adsorption-desorption equilibrium is reached. The adsorbed water-soluble pH substances can interact with the pH sensing layer 30, generating a potential difference between the working electrode and the reference electrode, based on which the pH vale of the gas sample can be measured. The water-soluble pH substances can be, but not limited to, ammonia, nitric oxide, nitrogen dioxide, hydrochloric acid, acetic acid or other organic acids.

Figure 4:
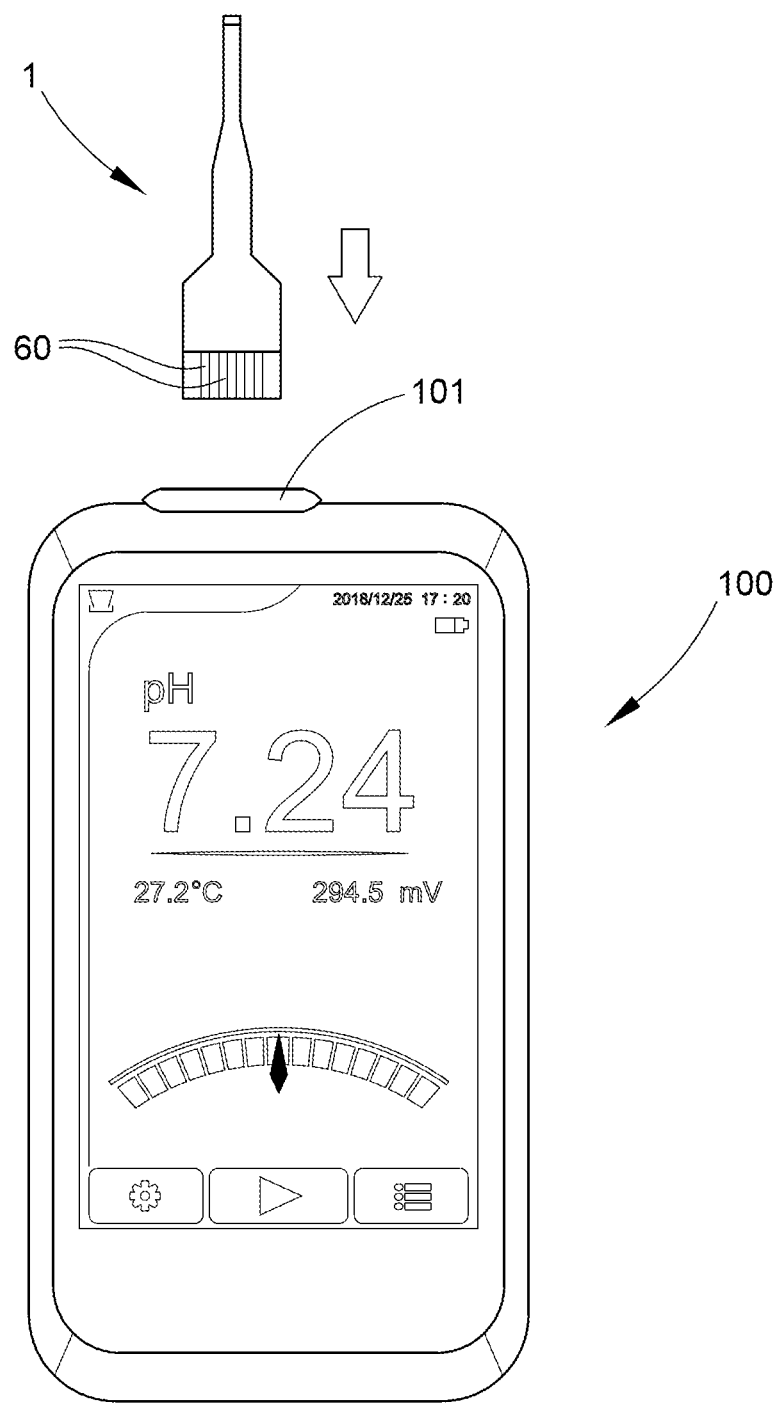
FIGS. 4 and 5 show applications of the first embodiment of the present invention.

Please refer to FIG. 4. The electrochemical test strip 1 can be used with a detector 100, which has a connection port 101 for the test strip 1 to insert therein. The connection port is formed with electrical contacts (not shown) capable of electrically connected to the gold fingers 60 so as to perform pH measurement. Alternatively, as shown in FIG. 5, the detector 100 can be provided with an extension adapter 110 for the electrochemical test strip 1 to electrically connect thereto so as to perform pH measurement.

Figure 6:
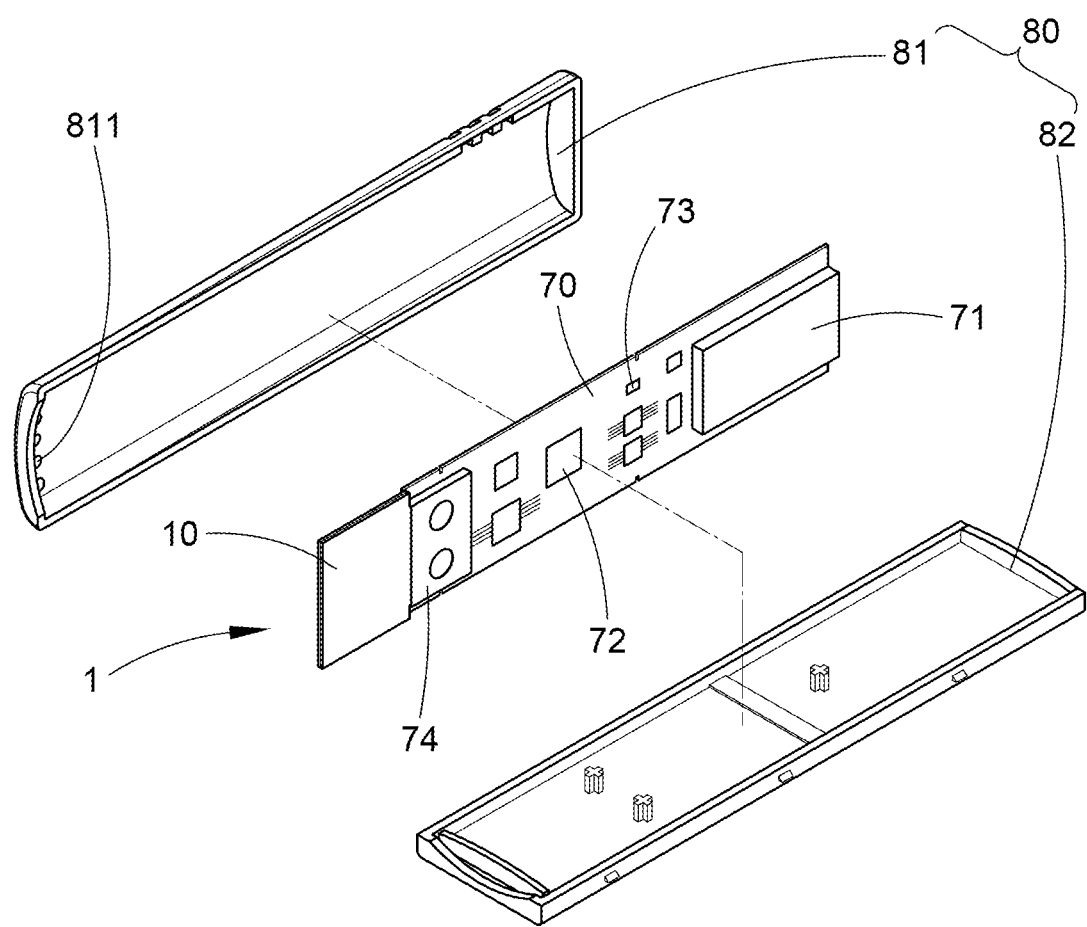
FIG. 6 is an explosive drawing of a second embodiment of the present invention.
Figure 7:
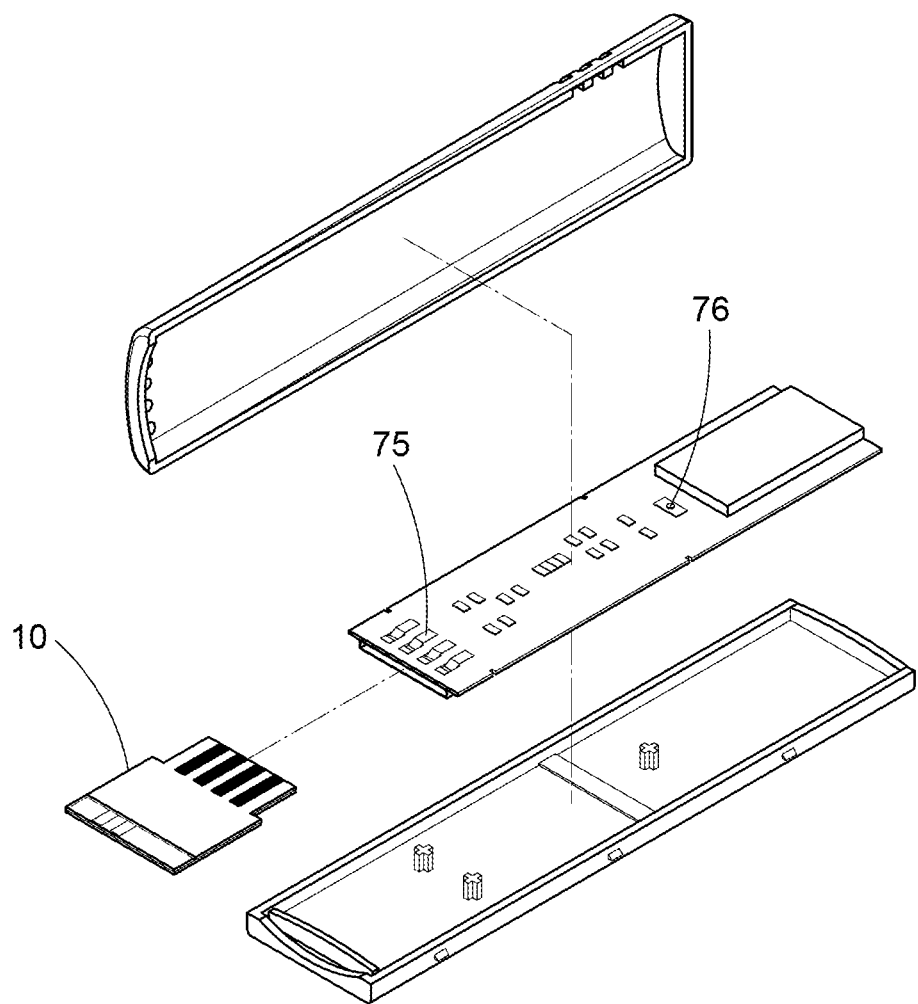
FIG. 7 is an explosive drawing of the second embodiment of the present invention in which the circuit board is shown at a different angle.

Please refer to FIGS. 6 and 7 for the electrochemical test strip of the second embodiment of the present invention. In addition to the parts shown in the first embodiment, the electrochemical test strip further includes a circuit board 70 and a casing 80. The circuit board 70 has a battery 71, a controller 72, an antenna 73, a strip slot 74, a plurality of strip contacts 75 and a switch 76, in which the battery 71, the antenna 73 and the strip contacts 75 are electrically connected to the controller 72, respectively. The antenna 73 is adapted to form a wireless signal connection with an external device, which can be a tablet computer 120 shown in FIG. 8 or other devices such as mobile phones and computers which can form a wireless connection with the electrochemical test strip 1 and can display, process and/or relay detection parameter signals. The strip slot 74 is adapted for the strip body 10 to insert therein. The strip contacts 75 can be, for example, jack strips. A part of every strip contact 75 is located in the strip slot 74 so that the gold fingers 60 of the strip body 10 can form electrical connection with the strip contacts 75, respectively. The switch 76 is adapted for controlling on/off circuit between the battery 71 and the controller 72. The casing 80 has a first casing part 81 and a second casing part 82 for encapsulating the strip body 10 and the circuit board 70. The first casing part 81 of the casing 80 has a plurality of air holes adapted for the gas sample to flow into the detection area.

Figure 5:
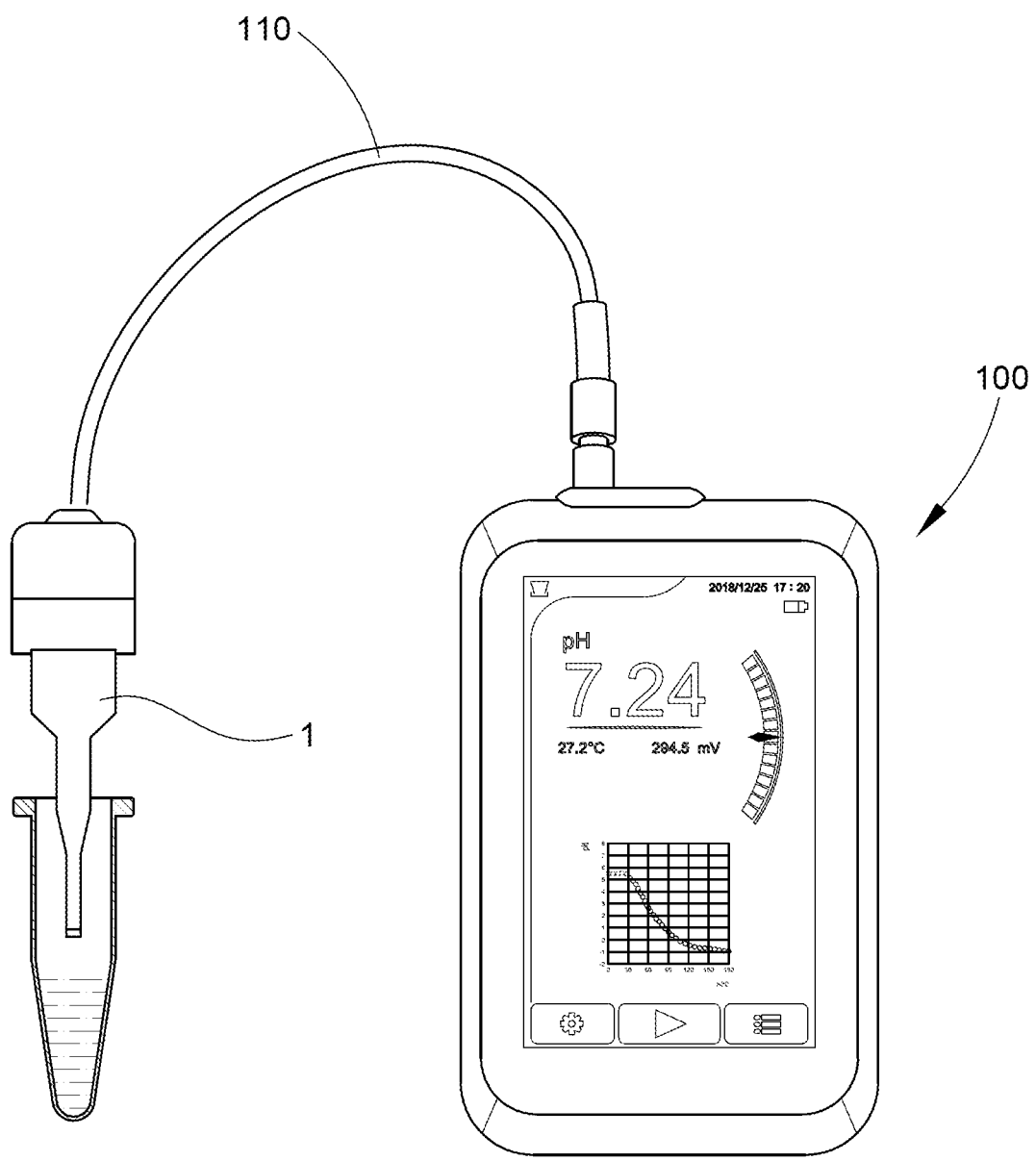
Figure 8:
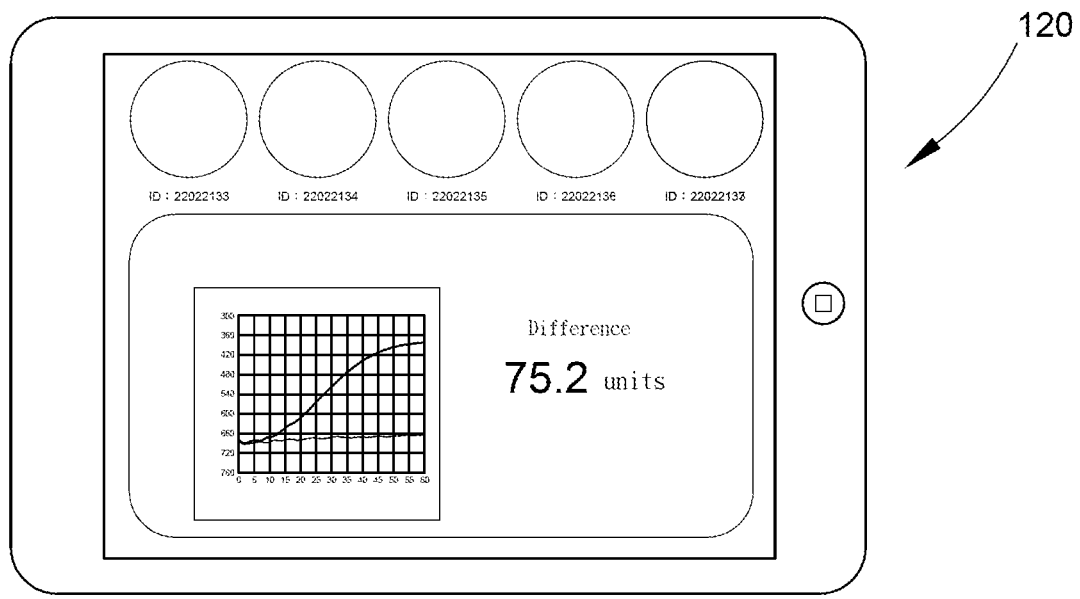
FIG. 8 is a drawing showing a tablet computer usable with the second embodiment of the present invention.

The electrochemical test strip of the second embodiment can perform the measurement of the potential difference between the working electrode and the reference electrode without the need the detectors 100 shown in FIGS. 4 and 5. The electrochemical test strip 1 of the second embodiment can be placed in a gas sampling bag 130 as shown in FIG. 9 to perform pH measurement and then transmit detection results to the device as shown in FIG. 8.

To verify the performance of the electrochemical test strip of the present invention, the following tests were conducted. Four samples, including 10% acetic acid aqueous solution, 10% hydrochloric acid aqueous solution, 5% ammonia aqueous solution and fish meat (stale meat can produce ammonia gas), were prepared. The electrochemical test strips were used to detect the volatile gases of the samples, individually, without direct contact with the samples. The test results are shown in FIGS. 10-13. According to the results, pH changes were not detected for a period of time at the beginning of the tests because the solid water absorption layer of each test strip just started absorbing/adsorbing water (in the form of water vapor) in the volatile gases and the absorbed/adsorbed water also took some time to gradually adsorb pH substances. After a short while, pH changes were noticeable and gradually became stable because the adsorption-desorption equilibrium was met between the water and the pH substances. The results show that the electrochemical test strips of the present invention can indeed detect whether there are pH substances in the gas samples and can reflect acidity/alkalinity of the gas samples.

Figure 9:
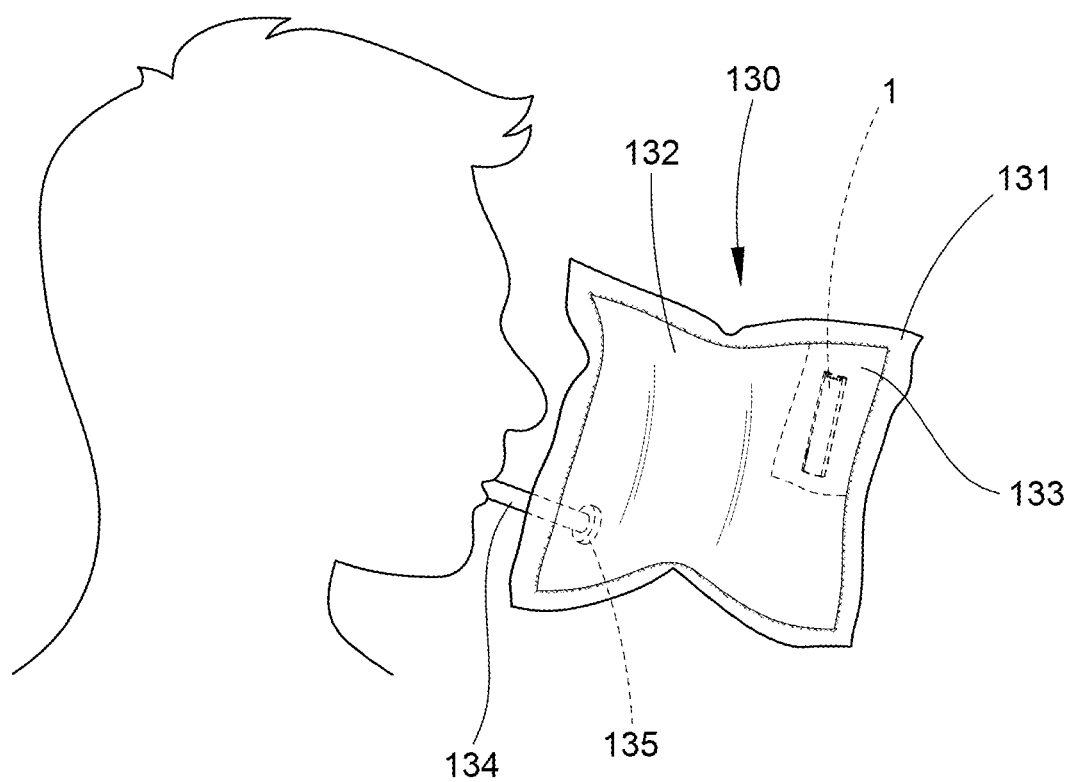
FIG. 9 shows an application of the second embodiment of the present invention.
Figure 9A:
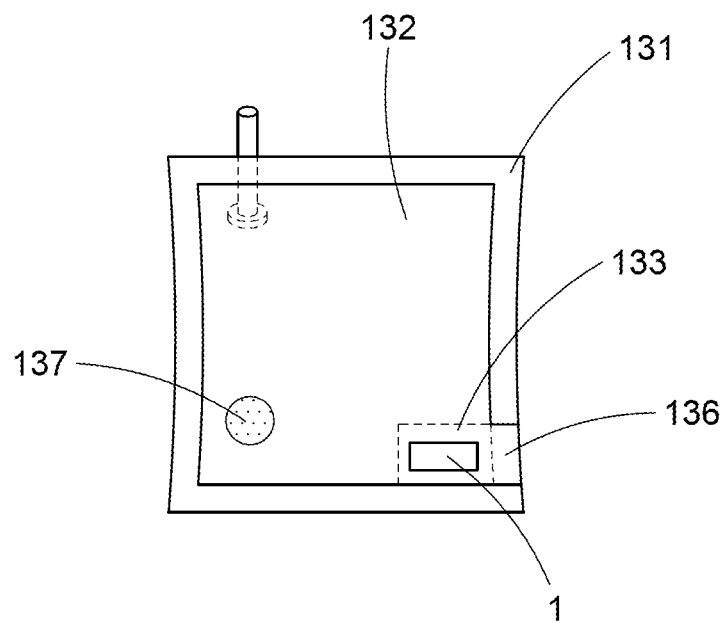
FIG. 9A is a drawing showing a gas sampling bag of a third embodiment of the present invention.
Figure 9B:
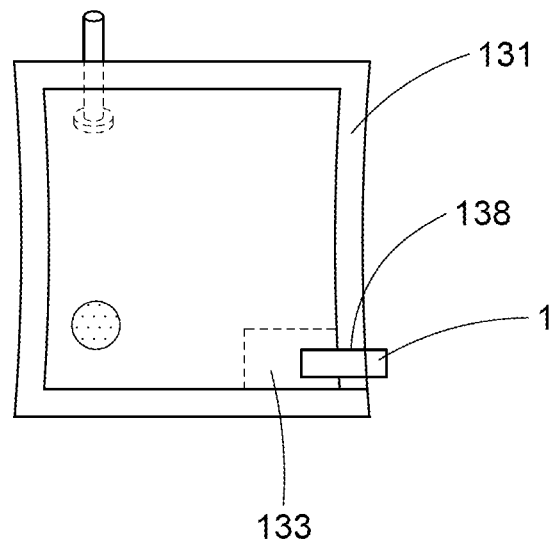
FIG. 9B is a drawing showing a gas sampling bag of a fourth embodiment of the present invention.
Figure 10:
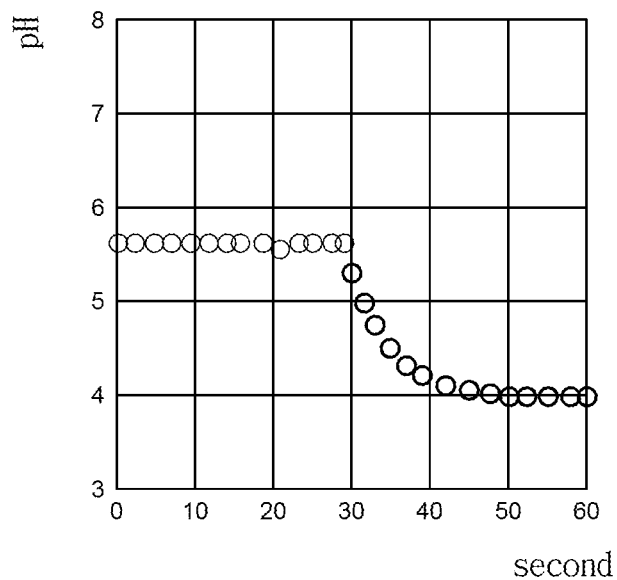
FIGS. 10-13 are graphs of experimental results of the gas pH measurement of the present invention.
Figure 11:
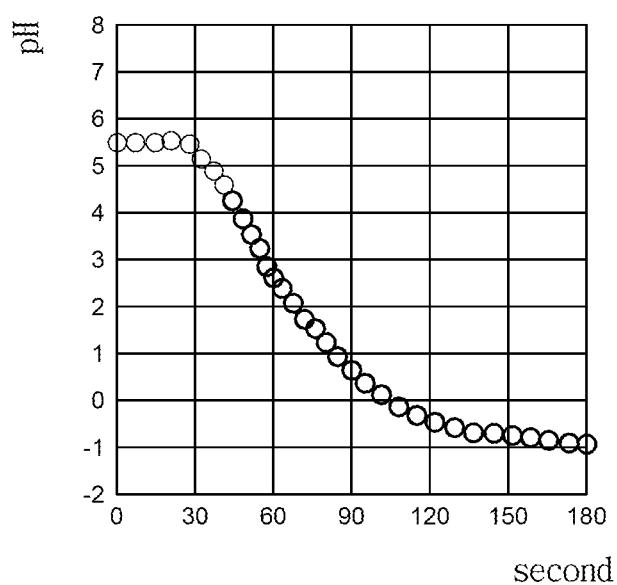
Figure 12:
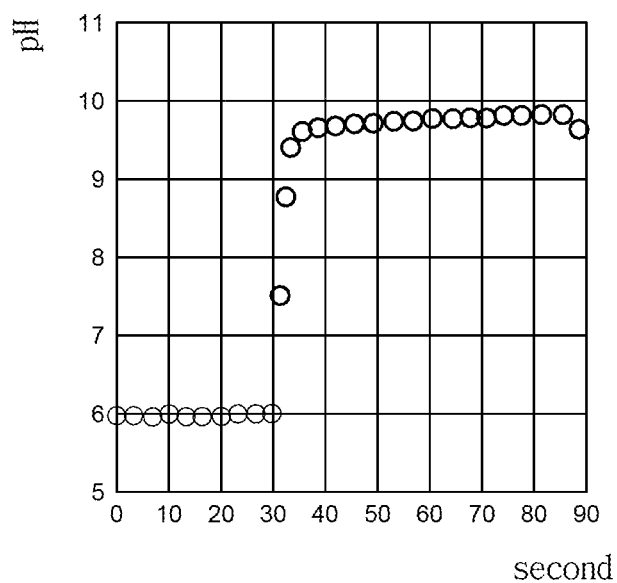
Figure 13:
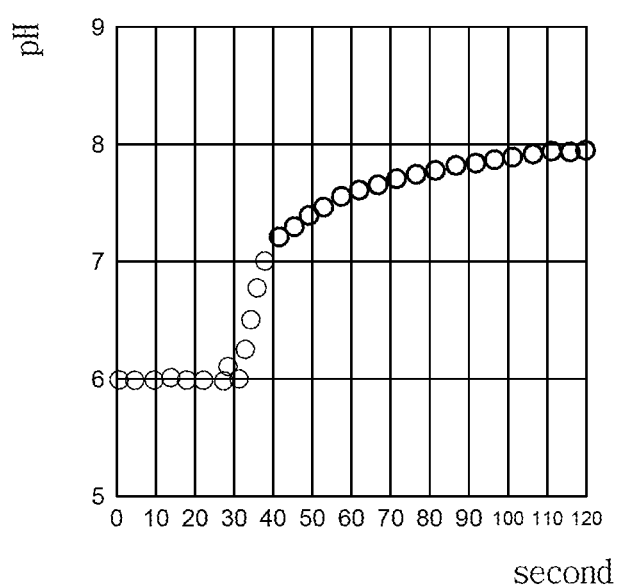

A method for detecting *Helicobacter pylori* using the electrochemical test strip is described as follows. *Helicobacter pylori* can survive in the human stomach and can secrete urea-decomposing enzymes to convert urea into carbon dioxide and ammonia. The converted carbon dioxide and ammonia can be excreted with exhalation, in which the ammonia can be detected with the electrochemical test strip of the present invention. The method includes the following steps:

as shown in FIG. 9, filling the gas sampling bag 130 with a first gas sample blown by a subject, and detecting the first gas sample with the electrochemical test strip 1 to obtain a background pH data; in order to mitigate test errors, the subject can fast for a period of time before the test; in the present embodiment, the gas sampling bag 130 includes a bag body 131, which has a main sampling chamber 132, a electrochemical test strip accommodating chamber 133, a blowpipe 134 and an oneway valve 135; the blowpipe 134 has a gas channel in communication with the main sampling chamber 132; the oneway valve 135 is disposed on the blowpipe 134 so that the gas sample is only allowed to flow in a direction from the gas channel to the main sampling chamber 132; the electrochemical test strip accommodating chamber 133 is in communication with the main sampling chamber 132 and is adapted to accommodate the electrochemical test strip 1; in the embodiment shown in FIG. 9, the electrochemical test strip 1 is embedded in the bag body 131; in the embodiments shown in FIGS. 9A and 9B, the electrochemical test strip 1 is replaceable; as shown in FIG. 9A, the bag body 131 has a selectively opened or closed pocket opening 136 in communication with the electrochemical test strip accommodating chamber 133; when the pocket opening 136 is opened, the electrochemical test strip 1 inside the bag body 131 can be replaced; in addiction, the bag body 131 further has a bleed valve 137 adapted to release the gas sample from the main sampling chamber 132, so that a single gas sampling bag 130 can be used for multiple times; as shown in FIG. 9B, the bag body 131 has a electrochemical test strip slot 138 in communication with the electrochemical test strip accommodating chamber 133; the electrochemical test strip slot 138 is adapted for the electrochemical test strip 1 to insert therein so that a part of the electrochemical test strip 1 is accommodated in the electrochemical test strip accommodating chamber 133; preferably, when the electro chemical test strip 1 is inserted into the electrochemical test strip slot 138 the electrochemical test strip 1 can make the electrochemical test strip slot 138 airtight; in other possible embodiments, the exposed part of the electrochemical test strip 1 can be mechanically connected to a detector (not shown);

then, feeding the subject with urea and waiting for a period of time, such as 15 minutes or more;

then, filling the gas sampling bag 130 with a second gas sample blown by the subject, and detecting the second gas sample with the electrochemical test strip 1 to obtain a desired pH data; the subject can use the same gas sampling bag 130 and the same electrochemical test strip 1 as the first sampling; alternatively, the subject can use a different gas sampling bag 130 and/or a different electrochemical test strip 1 if desired; if the same gas sampling bag 130 is used in the two samplings, the first gas sample needs to be released from the gas sampling bag 130 before the second sampling;

lastly, comparing the background pH data and the desired pH data to determine whether the subject's stomach has *Helicobacter pylori*.

Figure 14:
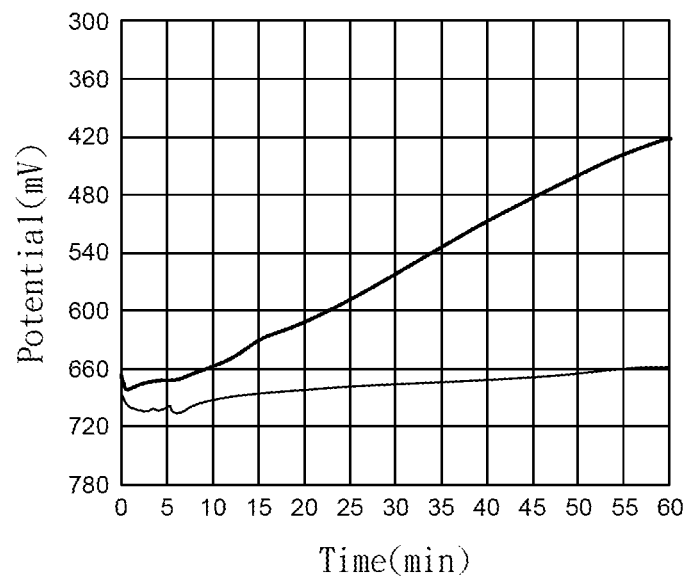
FIGS. 14-19 are graphs of experimental results that the present invention is applied to detect *Helicobacter pylori*, in which the thinner line represents a background pH data and the thicker line represents a desired pH data.
Figure 15:
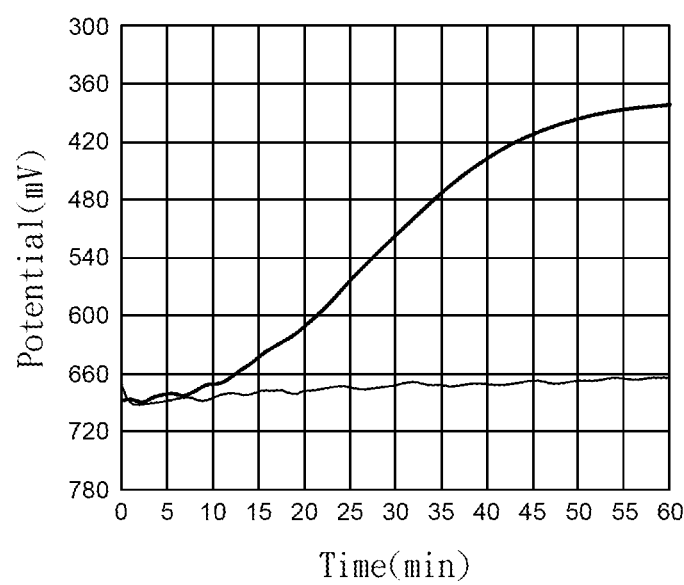
Figure 16:
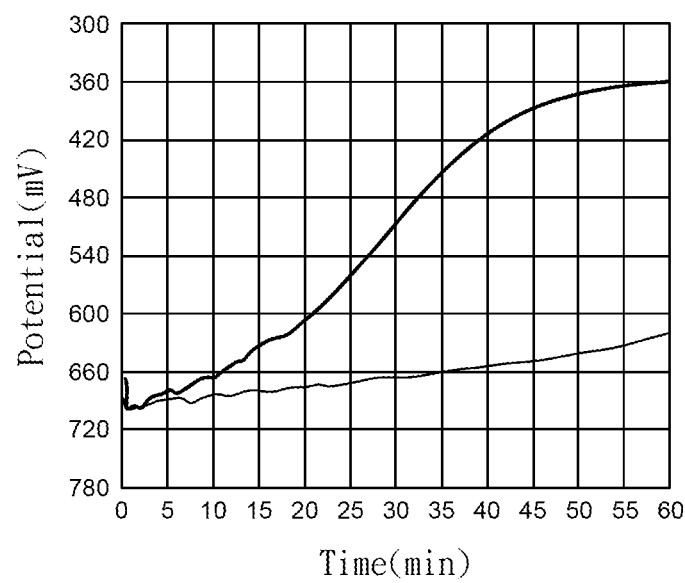
Figure 17:
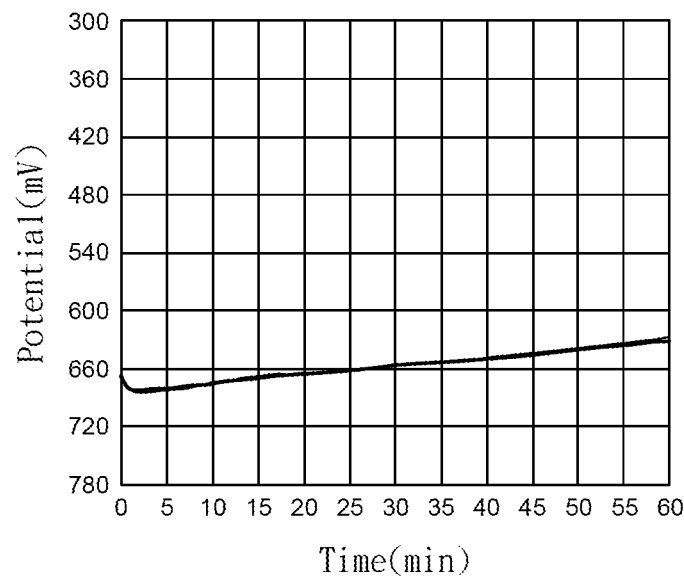
Figure 18:
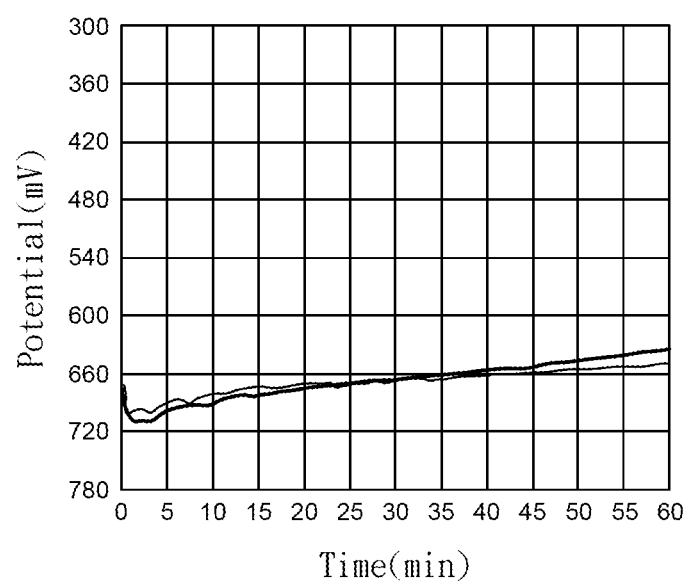
Figure 19:
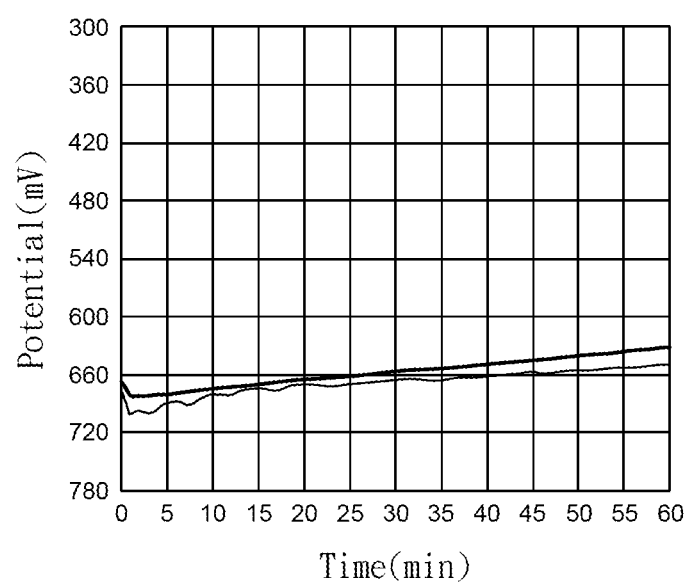

The applicant applied the aforementioned method on six subjects to determine whether the subjects were infected with *Helicobacter pylori*. In addition to the aforementioned method, all the subjects also took a conventional test for *Helicobacter pylori* (Carbon-13 Urea Breath Test) in a medical institution, in which three of them were found positive and the others negative. FIGS. 14-19 show the results of the aforementioned method performed by the six subjects. FIGS. 14-16 are the results of the three subjects who were found positive in the conventional test for *Helicobacter pylori*, in which there are obvious differences between the background pH data and the desired pH data and there are noticeable potential differences between the two data after a period of time. On the other hand, FIGS. 17-19 are the results of the other three subjects who were found negative in the conventional test for *Helicobacter pylori*, in which there are no obvious potential differences between the two data and the desired pH data substantially match up with the background pH data. It can thus be seen that the aforementioned method has high sensitivity and specificity for the detection of *Helicobacter pylori* in the stomach, and can quickly and accurately test whether the subject is infected with *Helicobacter pylori*.

What is claimed is:

1. A gas sampling bag for gas pH measurement, comprising a bag body, the bag body comprising a main sampling chamber, an electrochemical test strip accommodating chamber and a blowpipe, the blowpipe having a gas channel in communication with the main sampling chamber, the electrochemical test strip accommodating chamber being in communication with the main sampling chamber, and the electrochemical test strip accommodating chamber being adapted to accommodate an electrochemical test strip, the electrochemical test strip comprising:

a strip body, having a detection area for contact with a gas sample;

a working electrode, disposed on the strip body and having a first part located in the detection area;

a pH sensing layer, disposed on the first part of the working electrode located in the detection area;

a reference electrode, disposed on the strip body and having a second part located in the detection area; and a solid water absorption layer, disposed in the detection area and covering the pH sensing layer and the second part, the solid water absorption layer being adapted to absorb or adsorb water in the gas sample in a manner that the first and second parts are electrically connected to each other.

2. The gas sampling bag for gas pH measurement of claim 1, wherein the electrochemical test strip further comprises a plurality of gold fingers electrically connected to the working electrode and the reference electrode, respectively, the gold fingers are disposed on the strip body but not in the detection area.

3. The gas sampling bag for gas pH measurement of claim 2, wherein the electrochemical test strip further comprises a circuit board, the circuit board has a battery, a controller, an antenna, a strip slot and a plurality of strip contacts, the battery, the antenna and the strip contacts are electrically connected to the controller, respectively, the antenna is adapted to form a wireless signal connection with an external device, the strip slot is adapted for the strip body to insert therein, the strip contacts are adapted for form electrical connections with the gold fingers, respectively.

4. The gas sampling bag for gas pH measurement of claim 3, wherein the circuit board further has a switch for controlling on/off circuit between the battery and the controller.

5. The gas sampling bag for gas pH measurement of claim 4, further comprising a casing encapsulating the strip body and the circuit board, the casing comprising a plurality of air holes adapted for the gas sample to flow into the detection area.

6. The gas sampling bag for gas pH measurement of claim 1, wherein the bag body further comprises an oneway valve disposed on the blowpipe in a manner that the gas sample is only allowed to flow in a direction from the gas channel to the main sampling chamber.

7. The gas sampling bag for gas pH measurement of claim 1, wherein the bag body further comprises a bleed valve adapted to release the gas sample from the main sampling chamber.

8. The gas sampling bag for gas pH measurement of claim 1, wherein the bag body further has a selectively opened or closed pocket opening in communication with the electrochemical test strip accommodating chamber.

9. The gas sampling bag for gas pH measurement of claim 1, wherein the bag body further has an electrochemical test strip slot in communication with the electrochemical test strip accommodating chamber, the electrochemical test strip slot is adapted for the electrochemical test strip to insert therein in a manner that a part of the electrochemical test strip is accommodated in the electrochemical test strip accommodating chamber.

* * * * *